Figure 3:
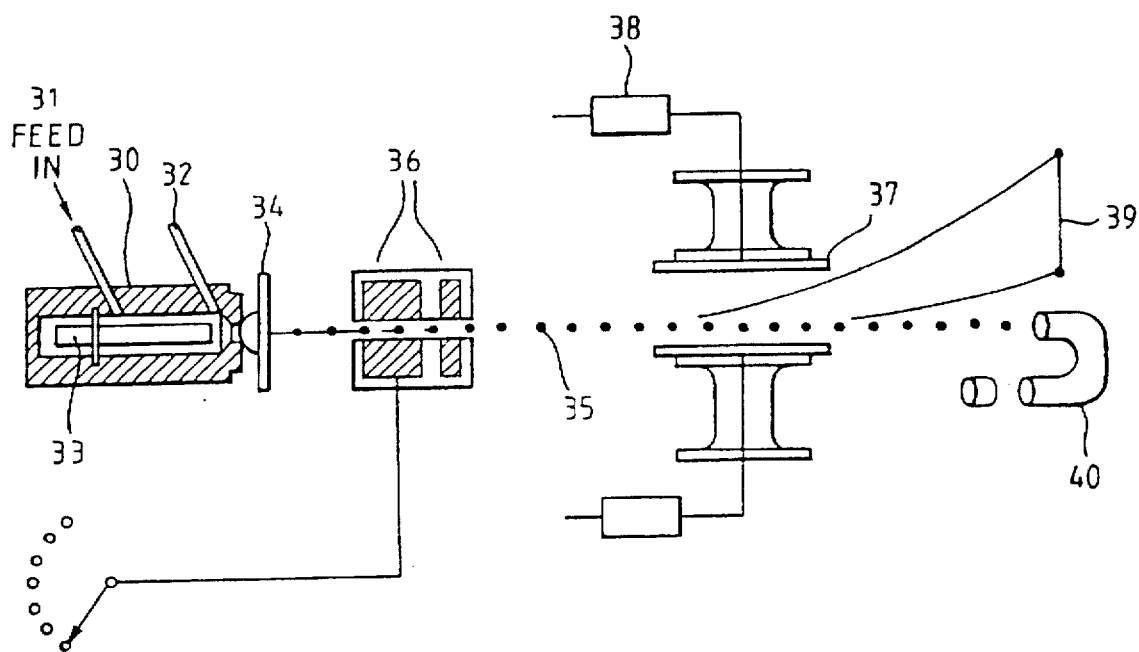

United States Patent [19]

Raybuck

[11] Patent Number: 5,763,170
[45] Date of Patent: Jun. 9, 1998

[54] METHOD FOR FORMING AN ARRAY OF BIOLOGICAL PARTICLES

[75] Inventor: Margaret Raybuck, Pont y Clun, United Kingdom

[73] Assignee: Amersham International plc, United Kingdom

[21] Appl. No.: 463,890

[22] Filed: Jun. 5, 1995

Related U.S. Application Data

[63] Continuation of Ser. No. 137,035, filed as PCT/GB92/00683, Apr. 14, 1992, published as WO92/18608, Oct. 29, 1992, abandoned.

[30] Foreign Application Priority Data

Apr. 16, 1991 [GB] United Kingdom ............... 9108066

[51] Int. Cl.$^6$ .................. C12Q 1/68; C12Q 1/70; G01N 33/53; C07K 13/00
[52] U.S. Cl. .................... 435/6; 435/5; 435/29; 435/32; 435/34; 435/39; 435/291; 435/801; 435/30; 435/309.1; 435/309.4; 435/7.1; 530/333; 530/334; 530/335; 530/350; 427/2.13; 209/3.1
[58] Field of Search ............... 435/29, 32, 34, 435/39, 291, 808, 30, 309.1, 309.4, 6, 5, 91.1, 7.1; 427/2.13; 209/3.1; 530/333–335, 300

[56] References Cited

U.S. PATENT DOCUMENTS

| | | | |
|---|---|---|---|
| 3,380,580 | 4/1968 | Fulwyler | 209/3.1 |
| 4,279,345 | 7/1981 | Allred | 209/3.2 |
| 4,347,935 | 9/1982 | Merrill | 209/3.2 |
| 4,361,400 | 11/1982 | Gray | 256/63 |
| 4,538,733 | 9/1985 | Hoffman | 209/3.1 |
| 4,565,783 | 1/1986 | Hansen et al. | 435/299 |
| 4,634,676 | 1/1987 | Sapatino | 435/294 |
| 4,959,301 | 9/1990 | Weaver et al. | 435/29 |
| 4,981,580 | 1/1991 | Auer | 209/3.1 |
| 4,988,619 | 1/1991 | Pinkel | 435/30 |
| 5,073,495 | 12/1991 | Anderson | 435/284 |
| 5,108,926 | 4/1992 | Klebe | 435/309.1 X |
| 5,410,412 | 4/1995 | Gombocz et al. | 356/326 |
| 5,483,469 | 1/1996 | van den Engh et al. | 435/30 X |

FOREIGN PATENT DOCUMENTS

| | | |
|---|---|---|
| 0 024 230 | 2/1981 | European Pat. Off. . |
| 0 119 573 | 9/1984 | European Pat. Off. . |

OTHER PUBLICATIONS

Shapiro, *Practical Flow Cytometry*, 2nd Edition, p. 110 (1988).

Primary Examiner—W. Gary Jones
Assistant Examiner—Dianne Rees
Attorney, Agent, or Firm—Wenderoth, Lind & Ponack

[57] ABSTRACT

A method for forming and using an array of, e.g., bacteria, yeast or bacteriophage for the purpose of identifying particular constituents thereof. The array is formed by directing a stream of droplets, each containing on average about 1 or a few biological particles, at spaced locations in an array on a surface, e.g., a nylon membrane or agar gel.

5 Claims, 2 Drawing Sheets

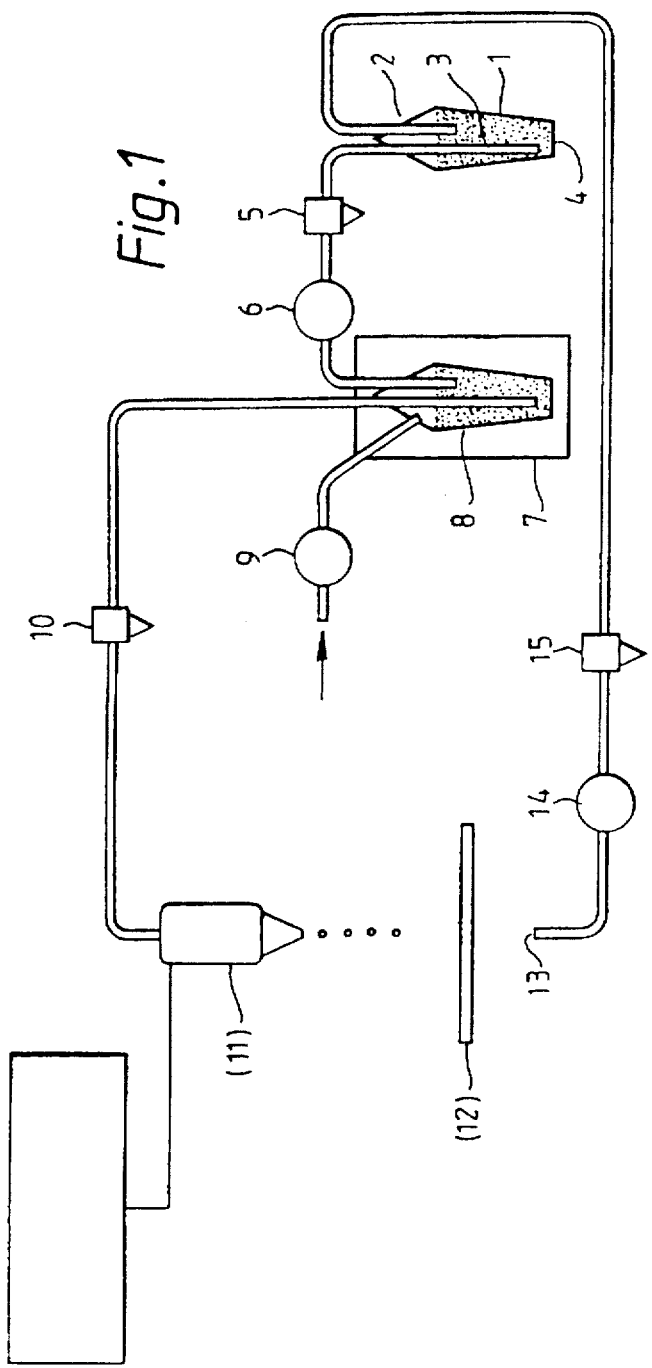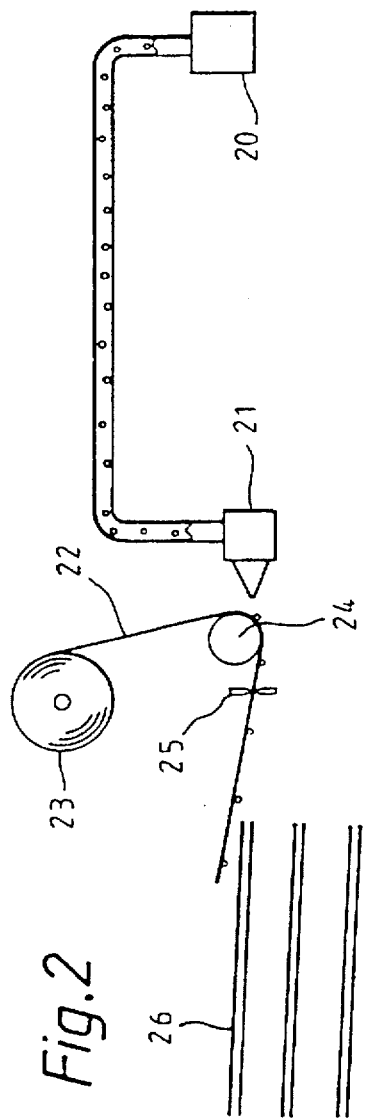

METHOD FOR FORMING AN ARRAY OF BIOLOGICAL PARTICLES

This application is a continuation of now abandoned application, Ser. No. 08/137,035, filed Oct. 18, 1993 now abandoned, which is the U.S. National Stage of PCT/GB92/00683, filed Apr. 14, 1992, published as WO92/18608 Oct. 29, 1992.

This invention relates mainly to the formation and use of arrayed clones of e.g. bacteria, yeast, bacteriophage etc. for the purpose of identification of particular constituents of the microbe such as DNA sequence, protein types etc. The invention also allows for the identification and subsequent retrieval of the desired clones for further analysis.

Analysis of clones i.e. identical collections of microbes is a powerful technique within molecular biology. It allows a fragmented length of DNA to be inserted piece by piece into a population of microbes such that each one has only one piece each. Each of the cells has to be allowed to grow up separately from all the others and then the particular DNA or protein etc. of interest has to be searched for using a tiny sample of each of these 'clones'. Alternatively naturally occurring populations of microbes may be searched for native DNA's or proteins separating each of the microbes within a population and then screening them all separately.

The customary practice is to flood a nutrient jelly in a dish within a thin layer of liquid containing the mixed-up population of microbes just as they have been found or made. After growth for a number of hours a small circular 'colony' arises made up of a large number of identical organisms all derived from the same single organism. It is very necessary to make sure that the culture is sparse enough to ensure that these colonies do not collide with each other as they grow. The amount of growth also must be limited or the colonies will eventually grow big enough to coalesce.

Each one of these colonies must then be transferred by touching the end of a sterile 'cocktail' stick into the centre and then touching onto a prepared substrate. This may be one of a number of possibilities such as a nylon membrane, an agar dish, or to liquid culture in a multiwell plate. Whichever method is chosen the colonies must be applied in such a way as to keep them permanently separate, for all future operations.

The next step is usually to make provision for duplicates of the original clones. This is an essential step for two reasons: firstly the process of screening the colonies usually involves breaking open the microbe to gain access to the DNA etc. This inevitably kills the organism. So in order to make it possible to retrieve positives a replica master must be available. Secondly the clones are not analysed for one constituent only, it may be desirable to look within the same population hundreds of times, so many replicas might be needed.

How this is done depends on what the initial substrate was used. If the clones are in liquid culture in microwells then a small amount of either the microbes themselves or their extracted DNA is removed and transferred onto a membrane sheet, using a toothpick or fine capillary etc. These constitute the duplicates and the microwells the master plate. If the original substrate was a membrane sheet then duplication may be done either by repeating the process of transfer from the agar culture onto further membrane sheets or by overlay. In this process a further sheet is laid gently and carefully over the original sheet and even pressure applied. This allows a tiny amount of material to transfer to the second sheet. If sufficient material is not present initially then the sheet may be incubated over nutrient agar.

Once the replicas have been made the master sheet or plate may be stored (e.g. freeze-dried or frozen). The replicas are then treated to fix the organisms to the substrate, and to burst them open. This reveals the nucleic acids and any proteins available within the microbe which may then be probed.

The probing is done by either DNA or RNA hybridisation, patterns of cutting by DNA restriction enzymes, immunochemistry using antibodies, polymerase chain reaction, or biological tests specific to the activity of the protein in question. In each of these methods final detection is by the signal from either a radioactive label or via the detectable chemical or physical properties of a chemical label (e.g. colour or light produced).

There are two opposing systems for the handling of DNA pieces depending on a number of parameters. For the utilisation of plasmids, cosmids or yeast artificial chromosomes, bacteria or yeast colonies are grown as described above. However there is another technology which many prefer to use which involves the culture of bacteriophage. These may have advantages for some applications but for the purpose of screening clones have a major difference. Rather than producing colonies of identical microbes, phage growing within bacteria eventually burst them open and release more phage. So rather than producing colonies they produce 'holes' within a lawn of host bacteria. They may then be replicated onto membranes as for colonies.

Choice of which of these systems is used depends on a variety of factors the most important being what size of fragment is being handled. Each of these manipulation systems has a different upper and lower size constraint.

It is evident that in particular the process of arraying the individual clones is extremely time-consuming on anything other than a very small scale basis. Table 1 shows the approximate numbers of clones required in analysis of the human genome (which is 1 000 000 000 bases in length). Not only are there very many human genomes to analyse but there are all the other species in the world many of which, especially the plants, have much larger genomes.

It is the object of the present invention to provide a method which is capable of producing ordered arrays of individual microbes at high speed, which will allow projects on a scale not hitherto feasible.

EPA 119573 describes apparatus for dispensing microdroplets of liquid reagent, innoculant or specimen in an array on an agar medium in a petri dish. But there is no teaching or suggestion that the contents of individual microdroplets may be different from one another.

EPA 24230 and U.S. Pat. Nos. 4,279,345; 4,347,935; 4,361,400; and 4,538,733 all describe cell sorting apparatus of the kind which form a succession of droplets each containing one or more cells, scanning each individual droplet and using the observation to deposit the droplet in one of a selection of containers. There is no teaching or suggestion to deposit the droplets in an array on a surface. And the present invention does not involve scanning each individual droplet.

In one aspect the invention provides a method of forming an array of different biological particles on a surface, which method comprises providing a supply of a liquid suspension containing a plurality of different biological particles, forming the liquid into a stream of droplets containing on average about 1 or a few biological particles per droplet, and depositing the droplets at spaced locations in an array on the surface, droplet formation and deposition being effected under sterile conditions.

TABLE 1

| Vector | Insert | No. of bacteria etc. necessary to array (Colonies/Plaques for Human Genome | Preferred time taken to array by this invention (minutes) | No. 20 × 20 Sheets | Time to array by hand (days) |
|---|---|---|---|---|---|
| Plasmid | Up to 10 KB | $1.4 \times 10^6$ | 40 | 70 | 350 |
| Cosmid | 30–40 KB | $5 \times 10^5$ | 15 | 25 | 125 |
| Phage | 10–20 KB | $7 \times 10^5$ | 20 | 35 | 175 |
| P1 | Up to 100 KB | $1 \times 10^5$ | 3 | 5 | 25 |
| Yeast Artificial Chromosome | Up to 500 KB or more | $2 \times 10^4$ | .5 | 1 | 5 |

The term biological particles includes microbes such as bacteria, yeast, bacteriophage, and also non-living macromolecules of biological origin such as genomic DNA, proteins, PCR amplification products, RNA, cDNA.

It will usually be necessary to bring the liquid suspension, usually by dilution, to a concentration such that each droplet thereof contains on average about one or a few biological particles. The optimum average number of particles per droplet is determined by statistical criteria, as discussed below, and is likely to be in the range of 1 to 10 or more.

The method may be performed by providing a reservoir to contain the liquid suspension of particles, all contained within a sterilisable housing, a mechanism for producing a stream of droplets of the liquid, a body having a surface to receive the stream of droplets, and means for directing and depositing individual droplets at spaced locations in an array on the surface.

The reservoir may be maintained at atmospheric, or lower or higher pressure (e.g. 250–350 kPa) according to valve requirements. There may be a thermostat to control the temperature of fluid in the reservoir and a stirrer to prevent settling out. The reservoir needs to be made sterilizable, and chemically inert both to the liquid suspension to be atomised and to any liquid used for cleaning or sterilizing between runs.

The liquid suspension passes from the reservoir to the droplet-producing mechanism via a tube that may include a filter, the pore size of which is chosen in relation to the biological particles being processed. For bacteria, a 5 μm filter may be appropriate to stop clumps of bacteria passing through and possibly blocking the droplet-formation mechanism. PTFE filters which will withstand up to 400 kPa are commercially available. This tube connects to a mechanism for the production of very small droplets. This may be either a high speed solenoid or a piezo-electric vibration device, with or without a fine nozzle (10–100 μm) to first obtain a stream. The stream of droplets may forced out of the head either by pressurising the system using an inert gas cylinder, from a compressor, or by raising the height of the reservoir. Or it may be done under atmospheric pressure and the piezo effect be solely responsible for shaking loose the droplet. Or it may be a localised heating device causes vaporisation adjacent to the orifice and hence sufficient momentary increase in pressure to eject a droplet. Each droplet contains one or more microbes this being adjusted by diluting the culture appropriately. There also may be a device to collect unplaced droplets and return them to the reservoir by a collection gutter operated by a peristaltic pump.

The device for placement of the droplets may either be by addition of a charge on each droplet which is then subject to electrostatic deflection or by movement of the head producing the droplet or a combination of both. The positioning of the drops is adjustable by altering either the deflection charge or the movement of the head or by increasing or decreasing the height between the head and the capture surface. These may be effected by a combination of microprocessor or computer control or manual interference.

It may be that the head is movable in two dimensions or that the head is stationary and the capture surface moves in two dimensions or the head moves in one dimension and the capture surface in the other dimension.

The surface onto which the drop is deposited may be a membrane or sheet material or the surface of a nutrient jelly or the cavities of a multi-well culture plate.

If a membrane, the capture surface may be arranged to feed into the apparatus from a continuous roll or be placed either automatically or manually as individual sheets. If nutrient jelly plates are used or microwell culture plates they may be added manually to the apparatus either single or in multiples on trays, or an automatic feed may be used.

Once deposition has occurred then continuous sheets may be cut up using a blade or guillotine and fed into a module. Either these or the individual sheets can be placed within a multi-shelved or racked incubation/humidification module. This can be either using specially prepared, nutrient incorporated membrane or untreated membrane such as nylon or nitrocellulose, which is overlaid onto nutrient jelly for the subsequent growth. If plates or dishes are used with pre-existing nutrients they may be placed directly in the incubation module. The incubation module may either be fitted with a heater and thermostatic element or may be removable to be placed inside a conventional incubator. In either case the module may be fitted with a humidification chamber or vessel filled with water to produce high humidity during incubation.

In another aspect, the invention provides a support for microbes comprising a fibrous membrane carrying a nutrient for the microbes. The fibrous membrane may be for example of polyamide e.g. nylon, nitrocellulose, PTFE, or even cellulose e.g. reinforced paper, provided the wet strength is high enough. The membrane should permit the passage through it of moisture.

The membrane carries a nutrient for the microbes, and is preferably impregnated with the nutrient as a result of having been dipped in a nutrient solution e.g. a sterile nutrient broth.

If these pretreated membranes are to be used they may be soaked in a solution containing sterile nutrient broth, antibiotic, tetrazolium dye, and then drained or dried and stored in sealed plastic folders. In use they may be used immediately if moist or they may be placed on humidified support layer such as filter paper to receive the drops. In either case they may be incubated in a dry incubator relying on this support layer for moisture which is essential for successful growth overnight. The size of the colonies may be adjusted by increasing or decreasing the level of humidity. This may be done either by altering the amount or availability of humidity in the chamber or by addition of supporting layers of varying number or degree of wetness.

Formation and deposition of droplets is effected under sterile conditions. The equipment may be contained in a sterilizable housing, e.g. a cabinet containing a UV sterilizing lamp or with provision for a sterilizing gas. The cabinet is closed during operation for safety reasons to avoid aerosol sprays of micro-organisms.

The liquid suspension of micro-organisms or other biological particles is diluted to an extent that each droplet will contain about one or a few organisms. Statistically to have a high likelihood of single organisms per drop then a high dilution would have to be employed which would result in a large preponderance of empty drops. For the large projects for which this application is suitable it would mean a huge excess. So a preferred strategy is to put down cells at a series of dilutions calculated to produce between 6 and 8 filled spots in 10. To achieve this in practice a stationary culture may be diluted by 1/1000. Problems arise when the organisms are probed for items of interest. Any positive 'clone' then has to be verified both for clonal origin and for fidelity. To verify the clonal origin a sample of the clone is taken and grown up a little and re-arrayed at the same dilution. Single occupancy of bacteria is then highly likely although if there is a need to establish this further then it can be repeated. Not only is this not a disadvantageous method it has positive advantages for particularly colossal projects. It allows a modest number of sheets to be used at, say, a theoretical level of 10 bacteria per drop or more. When the first analysis is then done identification of the desired microbe can be narrowed down to one collection of ten. These can then be grown up a little, resprayed and reselected on a modest number of sheets. If necessary this can be repeated until there is confidence that a single species has been attained.

Droplet size and droplet spacing depend on the equipment being used and on the method being preferred. It is necessary that droplets not coalesce, either on impact, or on bacterial growth during subsequent incubation of the array of deposits. In a large operation, it is advantageous that the droplets be as small as possible and that the array be as closely spaced as possible. A 60 μm nozzle can generate droplets of 1.5 nanoliters nominal volume, and smaller nozzles are possible. Bacterial growth during incubation can be controlled by limiting the available time or nutrient or moisture. Droplet spacings of a few mm are readily achieved and fractions of mm are expected.

The exact same apparatus can be used for the arrayed deposition of molecules also such as pieces of genomic DNA, proteins, PCR amplification products, RNA, cDNA etc. By adjusting the dilution factor deposition at the single molecule per drop can be achieved although by virtue of the Poisson distribution this is only statistically certain within limits.

After deposition on a suitable container which retains the spatial separation this then allows either screening by the methods outlined above or biochemical screens such as cDNA synthesis, biocatalytic conversions, PCR, or any screening assay.

The exact same apparatus can also be used to deposit microbes or molecules on the surface of a gel to which is subsequently applied a current leading to a spatial separation of the constituents of each droplet.

Reference is directed to the accompanying drawings in which:

FIG. 1 is a diagram of apparatus for performing the method of the invention;

FIG. 2 is a diagram of a different apparatus with more emphasis on the capture membrane;

FIG. 3 is a diagram of a device for producing and deflecting a stream of droplets.

The following description refers to FIG. 1.

The sample of microbes etc. is adjusted to the correct concentration to obtain a suitable confidence level of single entity per drop appropriate to the application. The sample is transferred into an autoclavable sterile container (4) which attaches to the port (2) of a low pressure reservoir (1) in a volume appropriate to the amount of spraying typically 5–20 mls. A flexible tube (3) made of a biocompatible plastic e.g. polythene, reaches to the bottom of the vessel which is also made of a biocompatible material such as polystyrene. The other end of the tube passes via a valve (5) with small internal dead space to minimise loss of material within the system, and a pump (6) into a pressure vessel (7). Inside the pressure vessel is an open sterile plastic container (8) which holds the sample. The pressure vessel itself is made of a thick perspex material which screws into a port on the machine. The vessel is pressurised by virtue of an attached gas supply of e.g. nitrogen or argon via a pressure gauge (9). Typically the pressure is at 250–350 kPa.

The material is moved from the reservoir (1) to the pressurised container (8) by the pump (6) which has non-return valves and is biocompatible e.g. by a bellows pump or HPLC-type pump. The material is passed via a valve (10) opening to a head (11) through polythene tubing. This head has within it a piezoelectric device and a charge allocation devices which both produces and charges up droplets.

Alternatively, any method of producing single droplets can be used here. Examples include high speed solenoid valves where the opening and closing of the valve causes drops to form.

Other possibilities are thermal or bubble jet mechanisms. In these low pressure systems a minute heating effect forces droplets out of an orifice by expansion of the liquid. Or similarly piezoelectric stimulation can be used to vibrate a droplet out of a nozzle.

The system of drop formation by piezotransducer under pressure can also be used and is based on formation by piezotransducer under pressure and charging and deflection according to the presence or absence of a fluorescence signal on the cell. (This enables drops not containing any microbe etc. to be discarded with drops containing microbes being deposited in an array as described on the capture surface).

In the first example of deposition by piezoelectric droplet formation and electrostatic positioning, either the capture surface or the nozzle head (11) additionally needs to move in the second dimension. Positioning in the first, linear dimension may be done by the electrostatics. In the second series of droplet formations, however where there is no inbuilt positioning mechanism the positioning of the drops on the surface may be done by mechanical movement of either the droplet producer (11) or of the capture surface stage (12). This can be done either by continuous movement of the capture surface or stepwise movement synchronised with the production of drops. There are a number of positioning tables commercially available which have the speed and accuracy to do this such as those sold by Laser Lines Limited.

A tube (13), pump (14) and valve (15) are provided to return to the reservoir (1) those droplets which have not been deposited on the capture layer. The return pump has a ceramic-coated internal space. A variable speed pump is used to allow optimal passage of cultures of varying viscosity and to reduce foaming in cultures containing protein material. The pump can be used at low speed to minimise foaming.

The capture layer (12) consists of either a sheet or a roll of material suitable to receive the microbial entities. Typically this would be made of a nylon, nitrocellulose, PTFE, or reinforced paper into which various combinations of nutrient media, antibiotics, dyes, bacteria, moisture, cryoprotectant, or enzymes have been incorporated in a variety of combinations appropriate to the application.

There is a variety of formats that this can include. Partly this varies as to application; a list follows:

1. Plasmid or cosmid (in bacteria).

The capture material may be allowed to absorb a nutrient solution such as Luria broth or any other medium for the growth of bacteria. Also contained in this solution may be an antibiotic such as ampicillin to prevent growth of undesirable bacteria, a dye such as tetrazolium red to reveal the growth of the bacteria, cryoprotectant such as glycerol to aid viability freezing.

2. Phage (bacterial virus)

The capture layer may have 'floppy' or soft agar soaked into it incorporating nutrient media, and a lawn of bacteria having been allowed to grow over the entire area.

3. Yeast

Yeast nutrient solution and appropriate antibiotics included and allowed to soak into the membrane.

In each of these cases either the membrane is allowed to remain damp or is dried for storage and then after arrays have been generated overlaid onto a moisture providing backing layer or put into a high humidity incubator. Alternatively the moisture layers may be bonded onto the rear of the capture sheets.

In each of these cases the capture sheets may be incubated in a warm place to allow sufficient growth to occur.

Subsequent treatments are standard practice involving replication of the arrays by any one of a series of possibilities and subsequent probing by complementary DNA or RNA hybridisation as usual.

FIG. 2 shows alternative apparatus for performing the invention. A liquid suspension of e.g. bacteria is maintained in a reservoir 20, and transferred from there to a head 21 which generates a stream of droplets each containing on average one bacterium. A capture membrane 22 is stored in continuous form on a roller 23 and led round another roller 24 where the individual droplets of the stream are caused to be deposited in an array on a surface. A guillotine 25 cuts the capture membrane into individual sheets which are loaded on collection trays 26, provided with a mesh interleave to protect the microbes on the surface, and inserted into an incubation module (not shown).

FIG. 3 is a diagrammatic representation of equipment for making and directing a stream of droplets. The equipment comprises a gun body 30, with a feed 31 for an aqueous suspension of biological particles, a bleed 32, a drive rod 33 and a nozzle 34 which generates a regular stream of droplets 35. A charge electrode 36 applies an electric charge to each droplet. A pair of high voltage deflector plates 37 controlled by a high voltage trip 38, deflects individual droplets within the range indicated by the line 39. A gutter 40 receives and recovers undeflected droplets of liquid.

As illustrated in FIG. 3, the equipment needs to be adapted:

by providing a sterile housing round the droplet formation and deposition equipment, to ensure that all surfaces in contact with the liquid suspension are of inert non-metal materials. Such materials are chosen, not only for biological compatibility, but also for resistance to corrosion by the salt solution invariably used in these experiments and by the alcoholic and other bactericidal/virucidal solutions used to sterilise the equipment between runs.

by providing a reservoir which is sterile and autoclavable.

by using valve with very small internal dead space.

by using a variable speed return pump to minimise foaming.

by providing a special surface to receive the droplets, which normally needs to be damp and to carry a suitable nutrient medium.

The following Examples illustrate the invention.

EXAMPLE 1 Arrays of phage libraries

A total genomic cDNA library of the yeast *Saccharomyces cerevisiae* was constructed using lambda arms as cloning vectors as follows. 1.5 ml of an overnight culture of *S. cerevisiae* DBY746 (Genetics 101, 387 1982) was placed in a microcentrifuge tube and the cells spun down and resuspended in 0.5 ml of 1M sorbitol, 0.1M EDTA. 25 µl Novozyme (Sigma) and 12.5 µl of 1M DTT was added and mixed by inversion. The suspension was incubated at 37° C. for 1 hr.

To these spheroplasted cells was added 30 µl of 10% SDS and the mixture was mixed by inversion. Lysis was completed by incubating at 37° C. for 5 mins. The mixture was purified by extracting with phenol/chloroform and chloroform alone and the DNA was then precipitated by adding an equal volume of isopropanol and holding at -20° C. for 30 mins. The pellet was washed with 70% ethanol and 300 µl water was added to the wet pellet. The tube was left open at 65° C. for 30 mins. allowing the pellet to resuspend and all residual alcohol to evaporate.

DNA concentration was checked by agarose gel electrophoresis and found to be in the region of 300 µg/ml.

Conditions for partial digestion of the DNA with the restriction enzyme Sau 3A were found as follows. To a microcentrifuge tube was added 150 µl of DNA, 52.5 µl water and 22.5 µl 10× restriction buffer. 15 µl of this mixture were dispersed into a series of microcentrifuge tubes on ice and 10 units of Sau 3A were added to 30 µl of the DNA mixture on ice. After mixing 15 µl was transferred to one of the other mixtures, mixed and then a further 15 µl was transferred to another tube to form a dilution series. This ensures that each microcentrifuge tube has exactly half the previous tube's concentration of enzyme for the same amount of DNA. All reactions were simultaneously incubated at 37° C. for 30 mins and then 65° C. for 5 mins. The reactions were then analysed by agarose gel electrophoresis and it was discovered that an enzyme concentration of 1.63 units/mg DNA gave partial digests with the majority of fragments migrating at a size of about 20 kb.

0.5 ml DNA was partially restricted by this method, checked by gel electrophoresis and layered onto a sucrose density gradient of concentrations 10–40% sucrose in 1M NaCl, 20 mM Tris pH8, 5 mM EDTA pH 8. The gradients were formed in polyallomer tubes by sequential addition and freezing of decreasing concentrations of sucrose. The gradients were thawed overnight at 4° C. and centrifuged for 19 hrs, 22000 rpm, at 20° C. in a SW41 swinging bucket rotor.

Fractions were collected, diluted one in two with water and run on an agarose gel in the presence of DNA size markers which contained equal amounts of sucrose. Fractions which contained DNA in the size range of interest were diluted ¼ with water and after the addition of ¹⁄₁₀ volume of 3M sodium acetate, 1 volume of isopropanol was added. Precipitation occurred at -20° C. overnight. The DNA was pelleted by centrifugation, washed twice with 70% ethanol and resuspended in water. By comparison with DNA concentration standards it was estimated that the Sau 3A digested DNA had a concentration of 300 µg/µl.

Lambda GEM 11 cloning arms, Bam H1 digested and dephosphorylated were purchased from Promega and following the kit instructions lug of arms were ligated to 1 µg of insert DNA in a volume of 10 µl. The ligation reaction was incubated at room temperature overnight. The ligation mixture was added to a Promega 'Packagene' extract for in vitro packaging again following the kit instructions and incubated at room temperature for 2 hrs. The extracts were suitably diluted and 100 µl of each dilution was added to 100 µl of log phase E. coli LE392. Infection occurred at 37° C. for 30 mins.

The infection mixture was added to 3 mls of top agar (1% tryptone, 0.5% NaCl, 0.01M MgSO$_4$, 1% agar) mixed and poured onto an LB agar plate (0.5% NaCl, 1% tryptone, 0.5% yeast extract, 1.5% agar). After the top agar had solidified the plates were incubated inverted at 37° C. overnight.

Examination of the dilution series revealed that the packaging mix contained $2.5 \times 10^6$ plaque-forming units/µg of arms. Assuming an average size insert of 15 kb, the number of clones required to have a 99% probability of complete representation of the haploid genome, estimated to be $2.3 \times 10^7$ base pairs is; 7000 phage particles (Maniatis). Therefore the library was deemed to be representative.

The library was amplified by adding 3 ml of phage buffer (20 mM Tris, pH 7.4, 100 mM NaCl, 10 mM MgSO$_4$) to the surface of a top agar plate confluent for plaque lysis. This plate was agitated for 4 hrs. at room temperature after the liquid containing the phage particles was aspirated off, cell debris removed by a brief spin at 4000×G and the particles stored at 4° C. over chloroform.

100 µl of a $10^{-1}$ and $10^{-2}$ dilution of this mix were added to 100 µl E. coli LE392 and incubated at 37° C. for 30 minutes to form the infection mix. 30 µl of molten top agar were cooled to 45° C. and 900 µl of log phase E. coli LE392 was added and mixed. This suspension of host cells was poured over the surface of a 20 cm×20 cm LB agar plate.

200 µl of the infection mix was added to 10 ml of sterile isotonic buffer which was put into the reservoir of the machine. The machine was used to deposit approx. 10 000 plaques per 20 cm×20 cm plate at an approximated spacing of 2 mm apart. The plates were then incubated, inverted at 37° C. overnight.

For analysis replicas were taken as follows. The plates were first allowed to harden at 4° C. for 1 hr. Hybond N filters were then placed over the surface of the plates for 1 minute. The filters, when lifted, contained library DNA from the arrayed plaques in a replica pattern. Five of these lifts were performed. Each was placed sequentially in denaturing solution, neutralising solution, and 2×SSC for 5 mins. each, dried on the filter paper at 68° C. and the DNA was cross-linked to the paper by exposure to UV light from a transilluminator for 30 seconds.

Probing of the library filters was done with two probes each containing a single copy yeast gene. One was ura 3 and the other trp 1. These were excised from their plasmids and purified on an agarose gel. The fragments were labelled with 32 P dCTP using an Amersham Multiprime kit according to the enclosed instructions. The fragments were purified by Sephadex g50 chromatography.

The Hybond filters were pre-hybridised in 200 mls Amersham Rapid Hybridisation buffer for 15 minutes at 68° C.

The radioactively labelled probes were denatured and added to the hybridisation mix. Hybridisation proceeded at 68° C. overnight. The hybridisation mix was poured off and the filters washed in 2×SSC for 2 mins. at room temperature and 0.1% SSC, 0.1% SDS for 15 minutes at 68° C. The filters were wrapped in Saran wrap and exposed to Amersham Hyperfilm autoradiographic film for 24 hours.

The resulting developed autoradiographs showed that for each gene there were approximately 2 copies per 10000 plaques which demonstrates that it is possible to obtain a truly representative plaque library using this invention. The clonal nature and correct assignment of these positives was checked by restriction digests and southern blotting that these were truly the appropriate single copy genes and not artifactual.

EXAMPLE 2 cosmid library arrays

A Schizosaccharomyces pombe cosmid library consisting of 3600 clones was a gift from the Imperial Cancer Research Fund. The cosmids were in bacterial host cells and so were diluted to concentrations of $10^{-1}$ and $10^{-2}$ in LB broth. A 10 ml solution was put into the low pressure reservoir of the machine. Spraying was done onto a capture layer suitable for cosmids. This consists of a sheet of nylon membrane into which has been impregnated LB broth, antibiotic (in this case kanamycin at 0.5 µg/ml) and tetrazolium red redox dye at a concentration of 1%. A mixture of these is made and nylon membrane immersed in the solution. The sheets are then dried before use.

The library was sprayed onto these sheets at a spacing of about 1 mm apart. The sheets were then put to incubate at 37° C. Probes of single copy S. pombe genes were obtained and labelled as in Example 1. These were S. pombe cdc 2 gene.

The sheets were replica plated using velvet pads and then fixed, denatured etc. as for Example 1 giving an autoradiograph with the same characteristics as Example 1, i.e. 3–4 positive clones per 10000. These were verified as for Example 1 by Southern blot analysis with the appropriate labelled probe and by restriction digestion to show clonality.

EXAMPLE 3 cDNA Libraries mRNA from human skeletal muscle cells was converted into a cDNA phage library by normal methods. A liquid suspension of the library was diluted as required, and the entire library arrayed on to 20,000 positions on a 20×20 cm plate of floppy agar containing host E. coli. The plate was then incubated overnight for the phage to lyse the bacteria forming plaques.

Lifts were then taken of these plaques onto nylon membranes, fixed and hybridised with 32P-labelled actin probes. (Actin is a single copy gene). Subsequent autoradiography of the membrane revealed positive spots where the actin gene sequence was found.

I claim:

1. A method of forming an array of different biological molecules on a surface, which method comprises providing a supply of an aqueous liquid containing a plurality of different biological molecules, forming the liquid into a regular stream of single droplets in a gaseous environment, said droplets containing on average at least one biological molecule per droplet, and directing and depositing each of said single droplets at a predetermined location spaced from other droplets such that said droplets form an array on the surface, droplet formation and deposition being effected under sterile conditions, said biological molecules being of the same type and said type being selected from the group consisting of genomic DNA, proteins, PCR amplification products, RNA and cDNA.

2. The method as claimed in claim 1, wherein after deposition the biological molecules are screened by a method selected from the group consisting of cDNA synthesis, biocatalytic conversions, PCR, hybridization and antibody binding.

3. The method as claimed in claim 1, wherein the surface comprises a gel.

4. The method as claimed in claim 3, which further comprises applying a current to the surface of the gel leading to a spatial separation of the biological molecule or molecules of each droplet.

5. The method as claimed in claim 1, wherein starting liquid suspension is diluted to a concentration such that a droplet thereof contains on average at least one biological molecule.

* * * * *